(12) United States Patent
Mitchell

(10) Patent No.: US 8,747,411 B2
(45) Date of Patent: Jun. 10, 2014

(54) FLUID DELIVERY AND BONE SCREW DRIVER APPARATUS

(76) Inventor: Michael David Mitchell, Spartanburg, SC (US)

( * ) Notice: Subject to any disclaimer, the term of this patent is extended or adjusted under 35 U.S.C. 154(b) by 190 days.

(21) Appl. No.: 12/895,845

(22) Filed: Sep. 30, 2010

(65) Prior Publication Data

US 2011/0245881 A1 Oct. 6, 2011

Related U.S. Application Data

(60) Provisional application No. 61/277,875, filed on Sep. 30, 2009.

(51) Int. Cl.
*A61B 17/58* (2006.01)

(52) U.S. Cl.
USPC .......................................... 606/104; 606/304

(58) Field of Classification Search
USPC ...................... 606/92–95, 104, 300–331, 916
See application file for complete search history.

(56) References Cited

U.S. PATENT DOCUMENTS

| 6,048,343 | A * | 4/2000 | Mathis et al. | 606/916 |
| 6,214,012 | B1 * | 4/2001 | Karpman et al. | 606/93 |
| 2004/0225292 | A1 * | 11/2004 | Sasso et al. | 606/73 |
| 2005/0015061 | A1 * | 1/2005 | Sweeney | 604/264 |

* cited by examiner

*Primary Examiner* — Nicholas Woodall
(74) *Attorney, Agent, or Firm* — Thomas A. O'Rourke; Bodner & O'Rourke, LLP

(57) ABSTRACT

A fluid delivery and bone screw driver apparatus attaches to a bone screw. An inner sleeve joins a material delivery source connected to one end of the inner sleeve to the bone screw connected to the other end. A removable liner communicates the material through the inner sleeve and into the bone screw. An outer sleeve seals the outer sleeve to the head of the bone screw. Rotating the outer sleeve tightens the seal and rotates the bone screw.

14 Claims, 9 Drawing Sheets

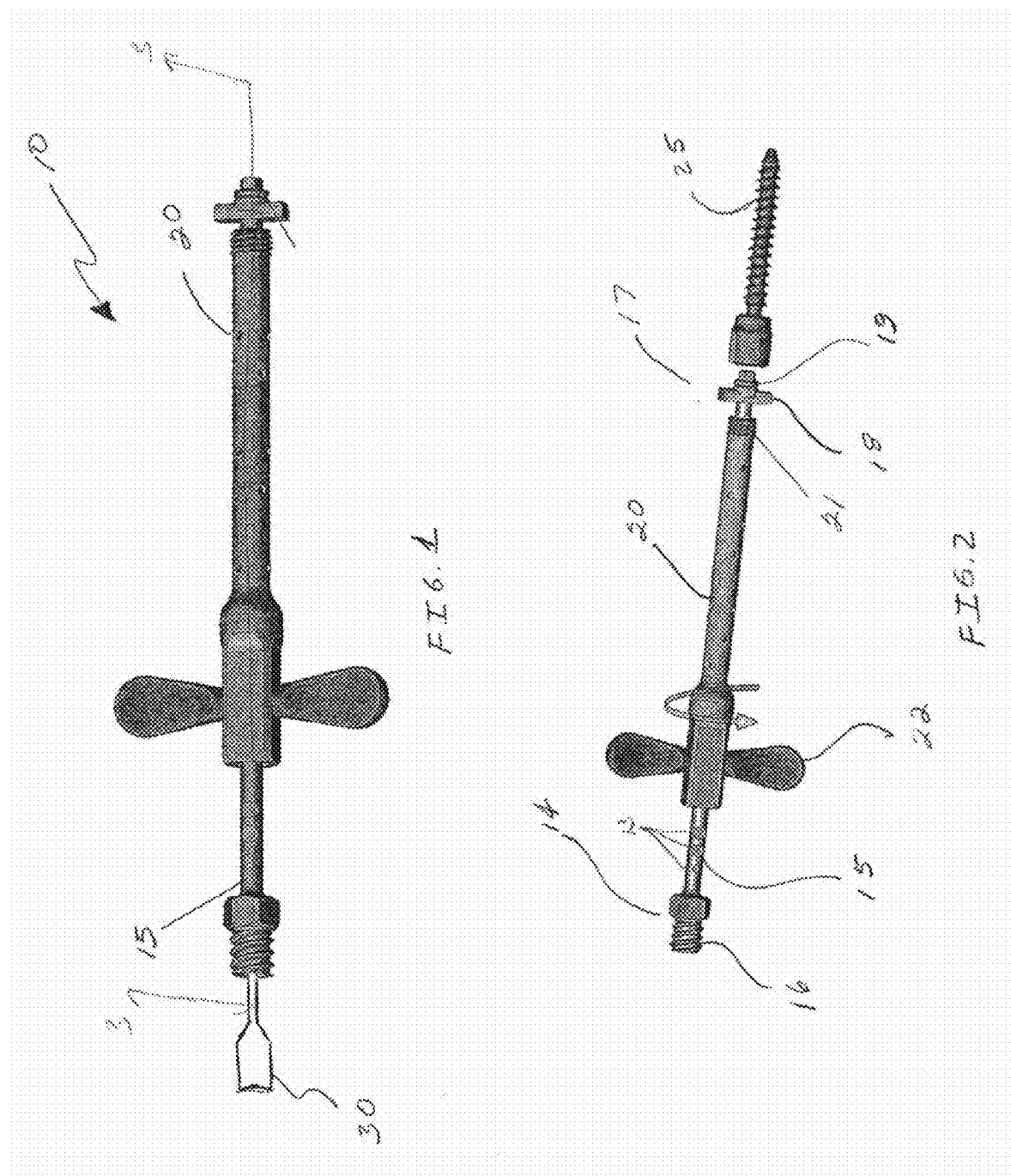

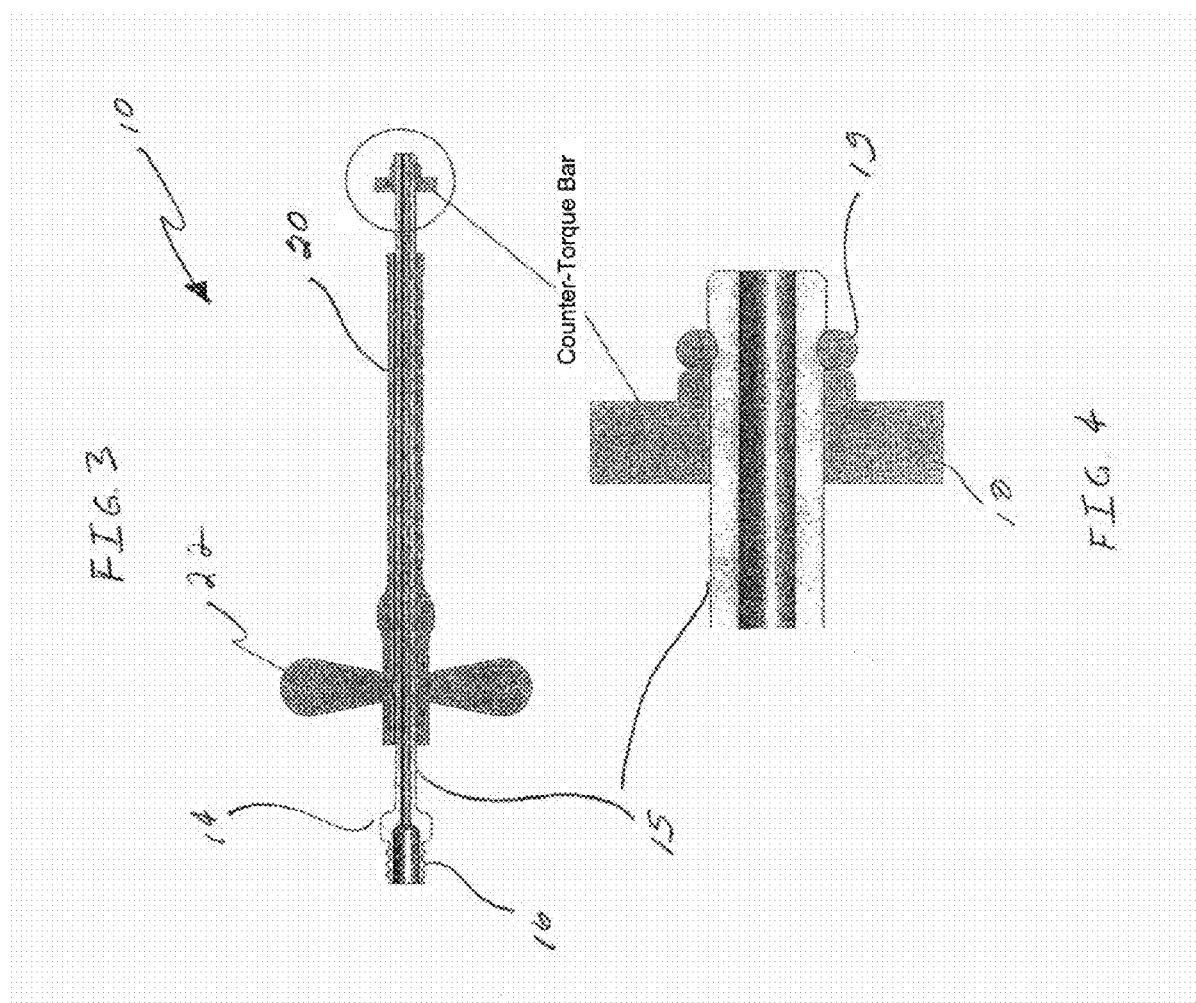

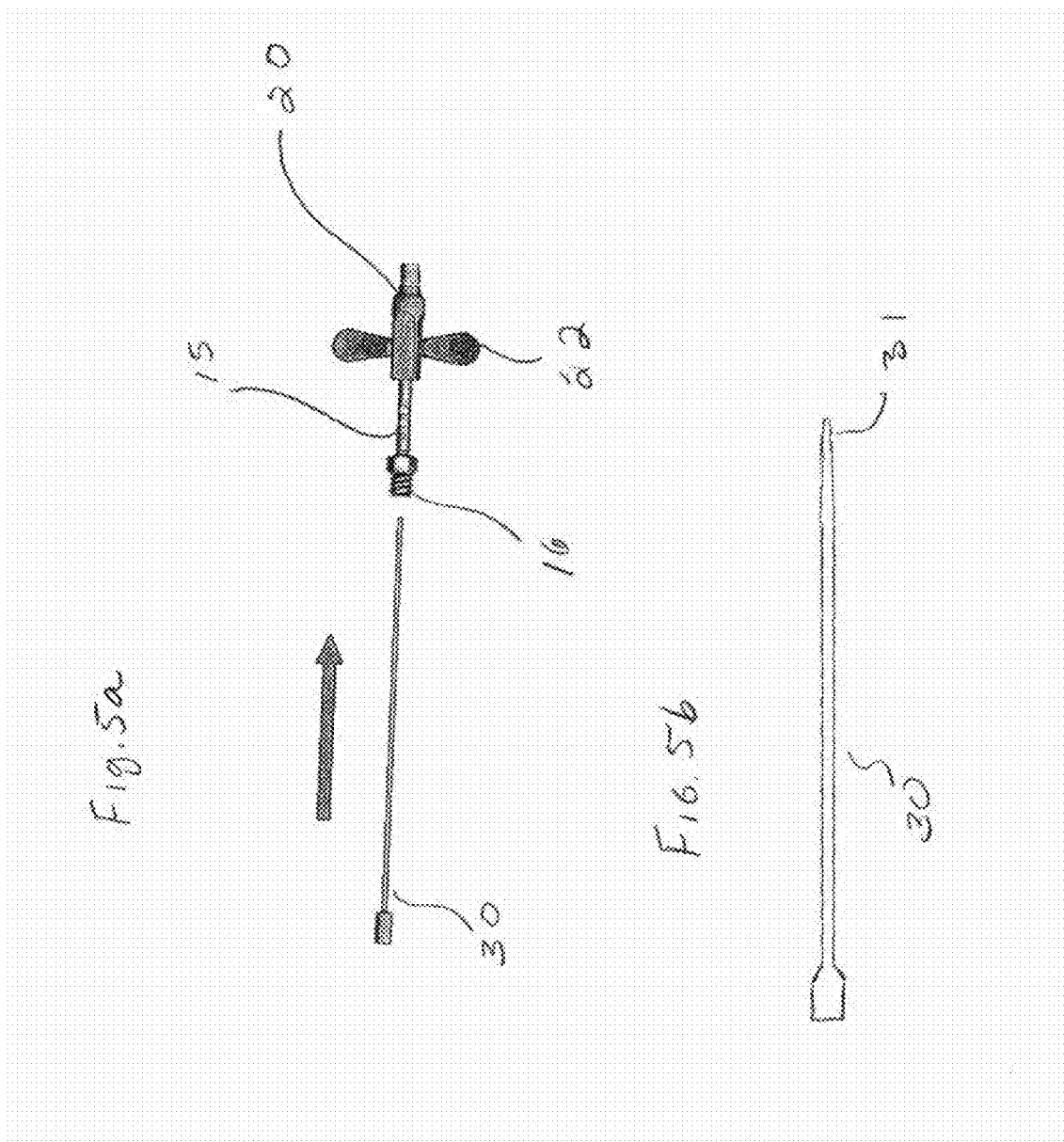

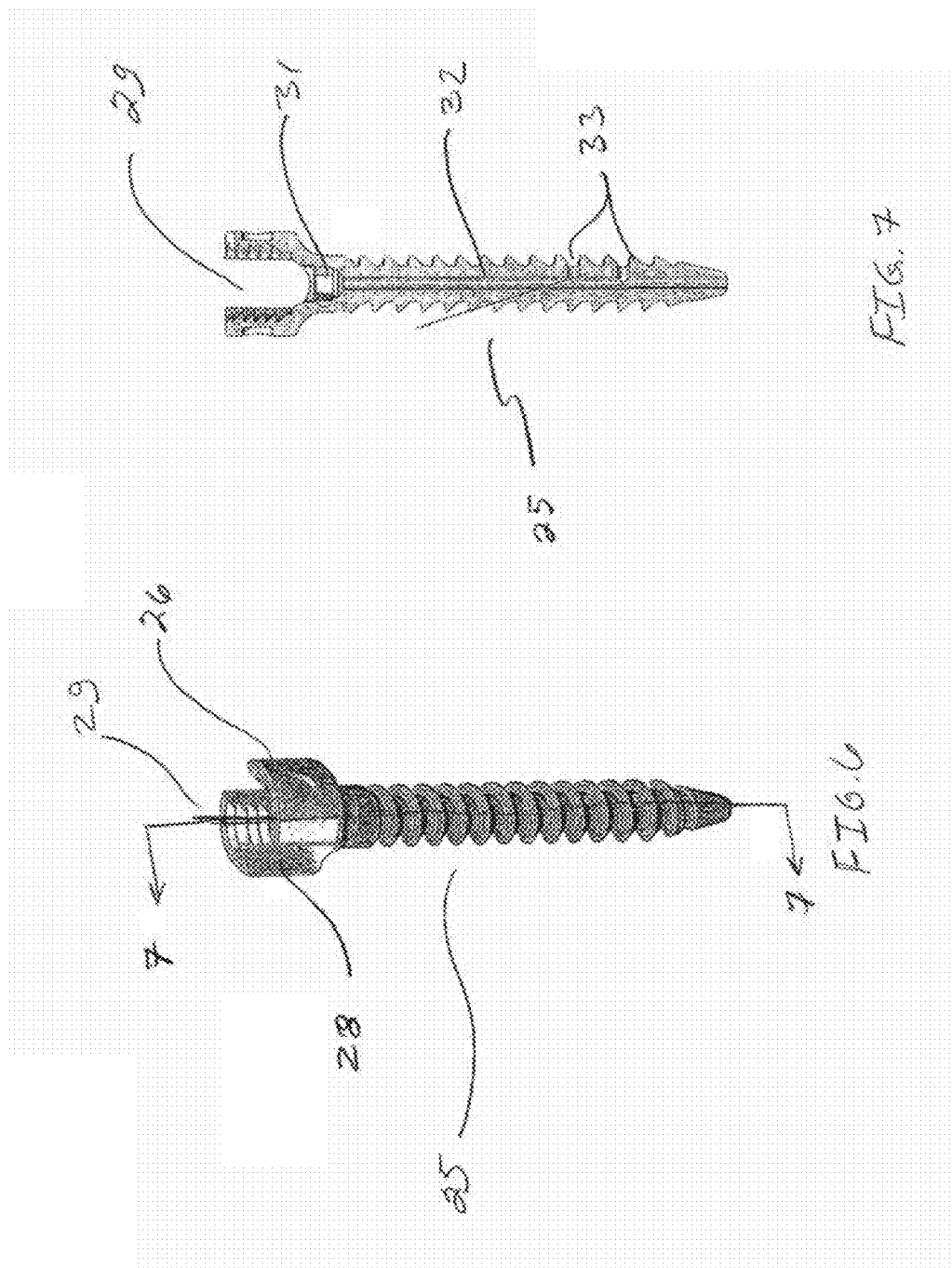

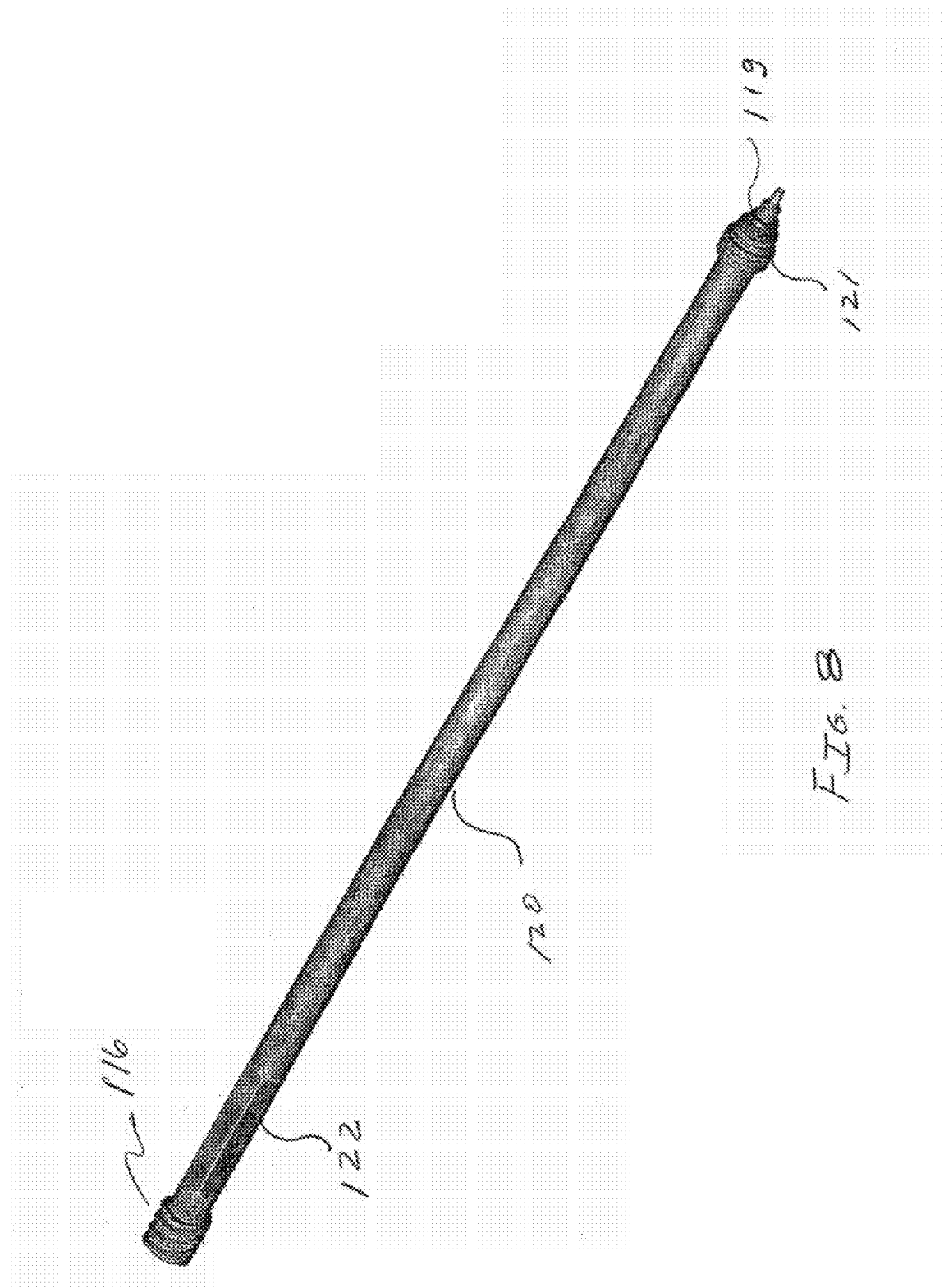

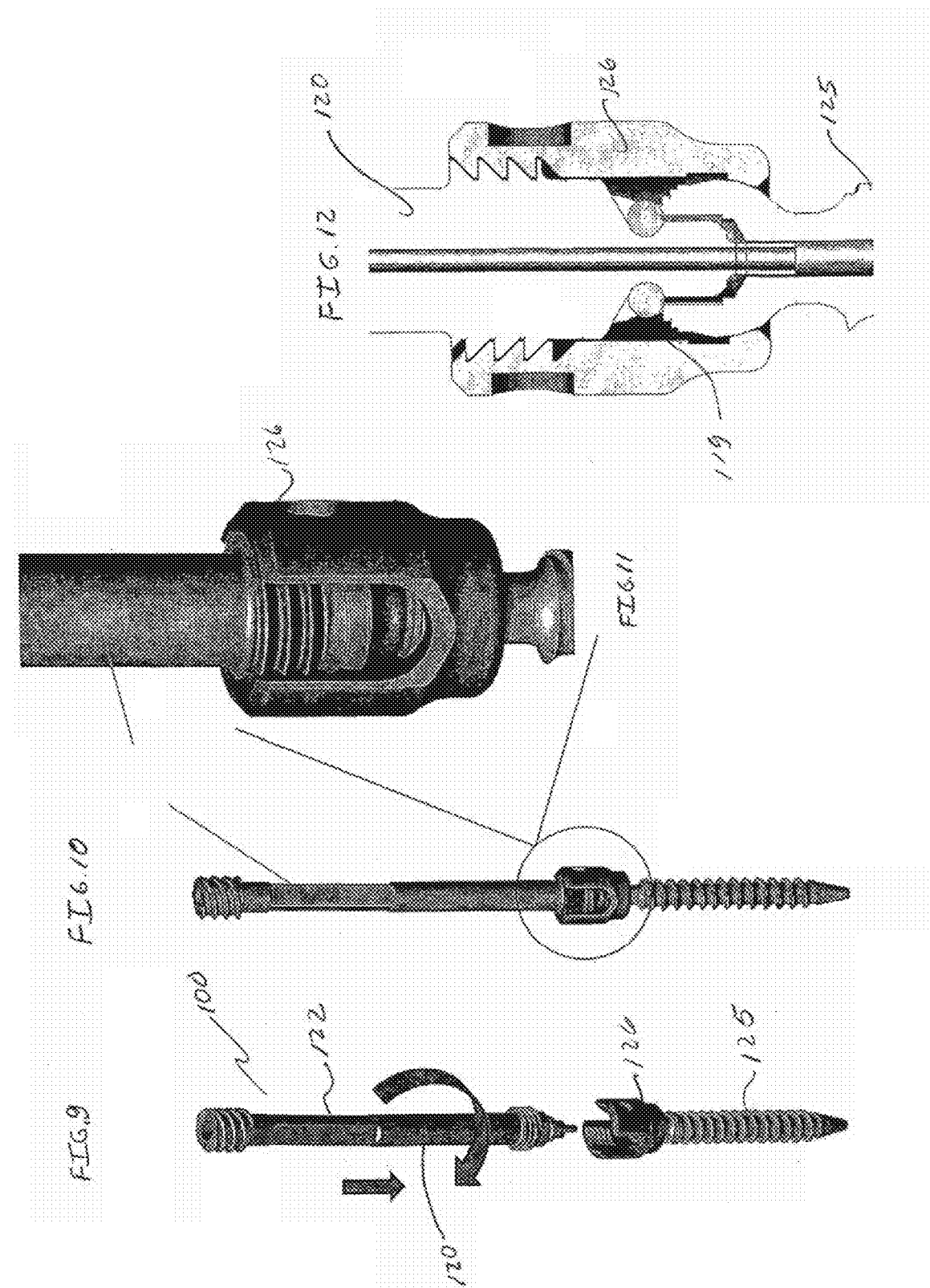

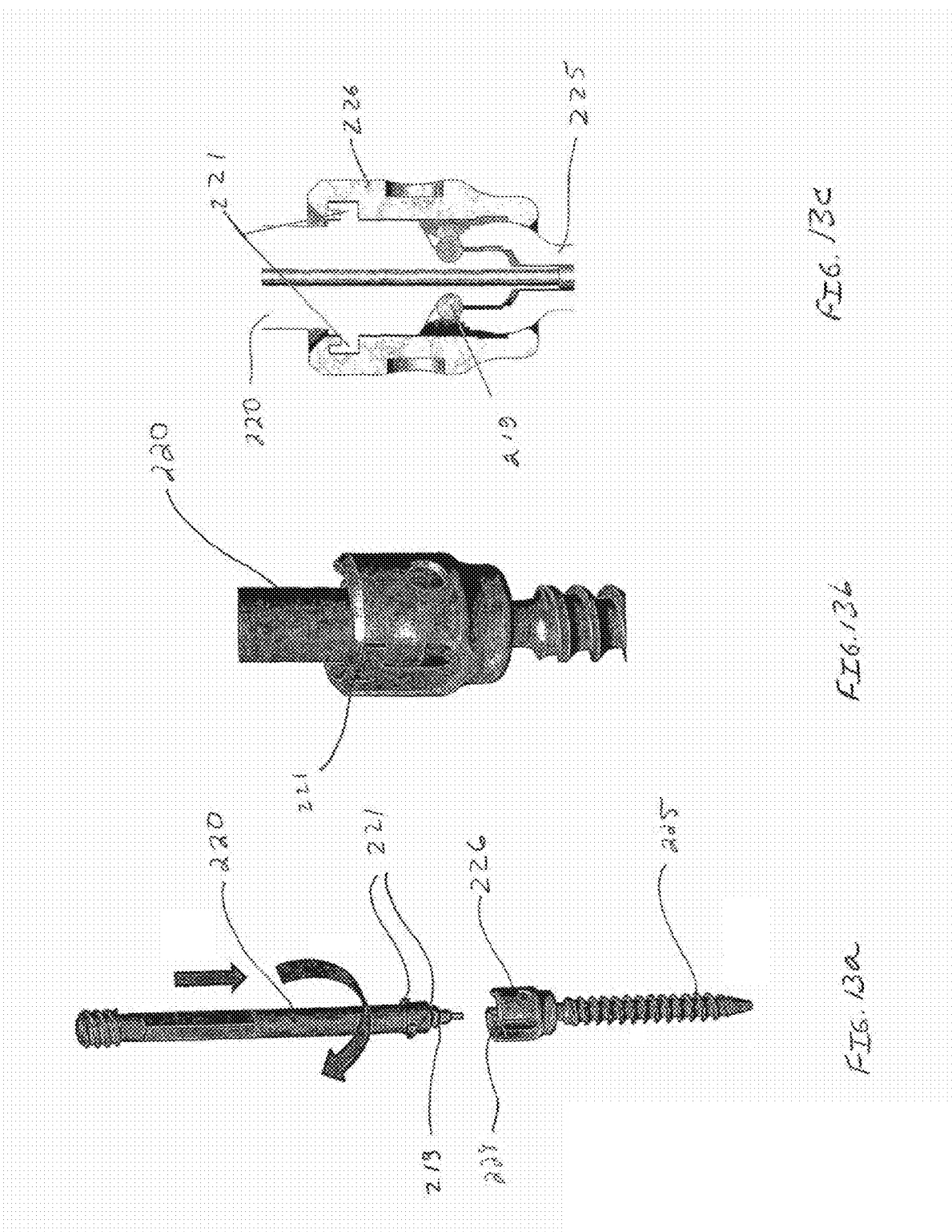

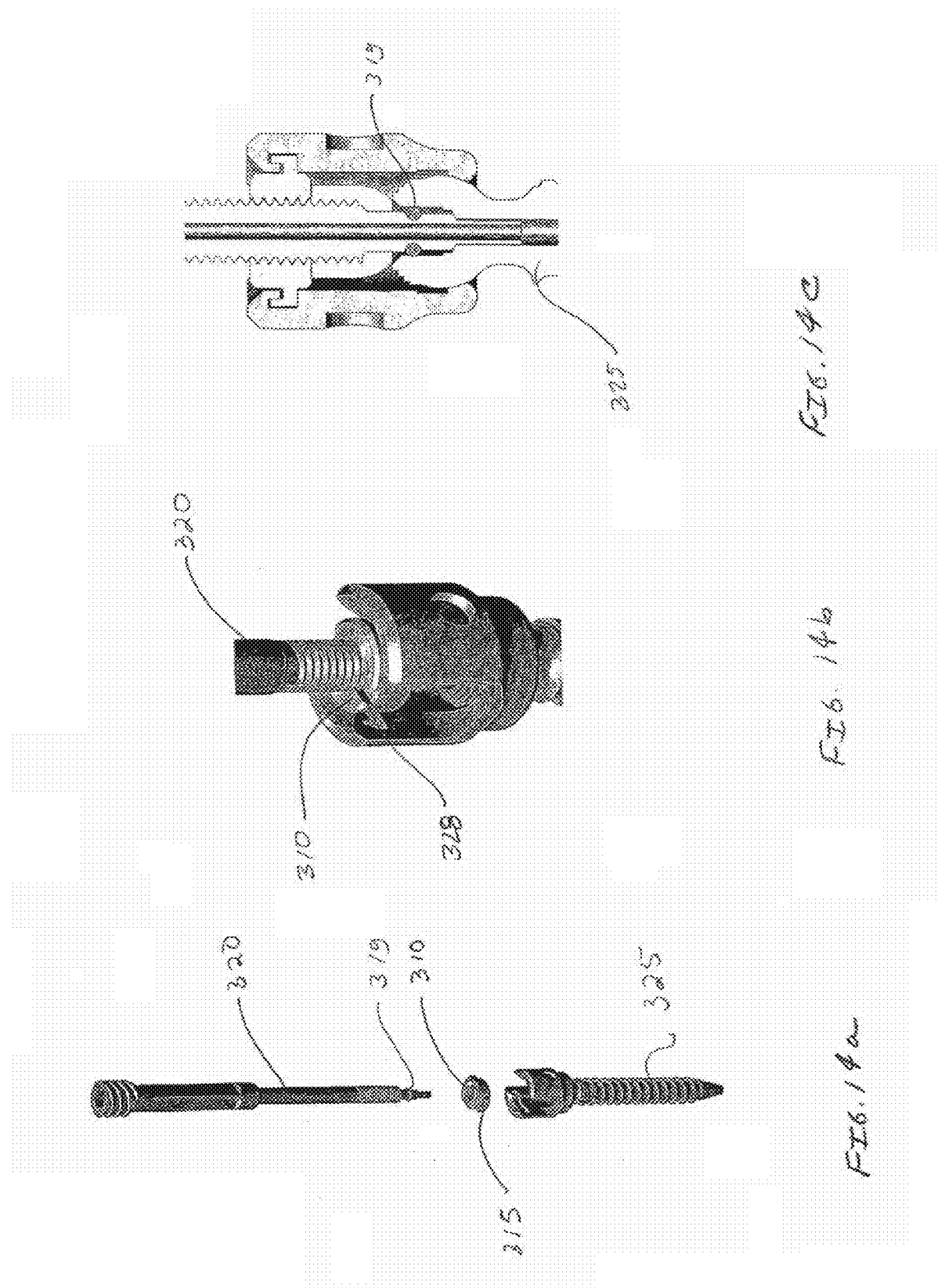

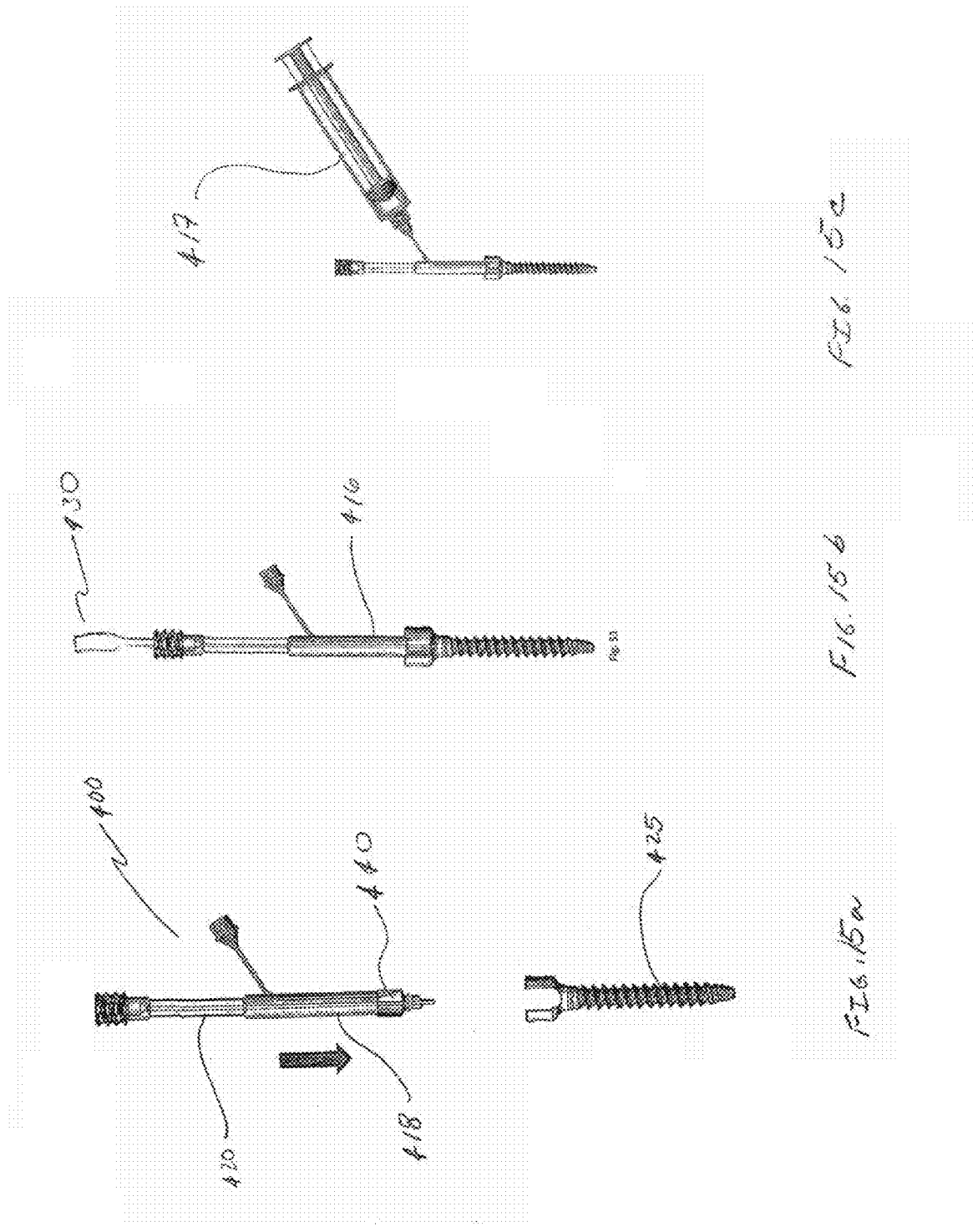

FLUID DELIVERY AND BONE SCREW DRIVER APPARATUS

This application claims the benefit of U.S. Provisional Application No. 61/277,875, filed Sep. 30, 2009, which is hereby incorporated by reference.

BACKGROUND

Spinal stabilization procedures typically involve inserting a pedicle screw into the pedicle or pillar of the spine, and then connecting the screw to either plates or rods for stabilization of the lumbar spine for fractures, tumors, and various degenerative conditions. When this procedure is used on osteoporotic patients the pedicle screw is sometimes difficult to fix because the threads of the pedicle screw do not properly secure within the material of the pillar. This is also a problem with non-osteoporotic patients when attempting to secure surgical anchors within the material of other skeletal members. To help achieve proper fixation of screws in osteoporotic skeletal structures, a fenestrated screw is used in conjunction with a cementitious material to provide a better footing for the screw and achieve enhanced bone fixation.

To achieve this fixation, current techniques often use a driver that is removably attached to the screw and is used to place the screw in a determined location. Once the pedicle screw is in place, the driver is undocked from the screw and a delivery device for the cement is docked to the head of the screw. Percutaneous fenestrated screw procedures are very difficult to perform with current technologies because the process of removing the driver from the screw and attaching a delivery system is often very arduous.

SUMMARY

A fluid delivery and bone screw driver apparatus attaches to a bone screw. The bone screw has a head and shaft. The shaft has a cannula with fenestrations. An exemplary bone screw is disclosed in U.S. patent application Ser. No. 11/736,943, filed Apr. 18, 2007, which is hereby incorporated by reference.

The apparatus comprises an outer sleeve having a proximal end and a distal end with external threads near the distal end and a grasping surface near the proximal end. And inner shaft having a proximal end and a distal end extends through the outer sleeve. The inner shaft comprises a coupler at the proximal end, a counter-torque bar at the distal end, and a gasket at the distal end. A removable liner extends through the proximal end of the inner shaft and out of the distal end of the inner shaft.

BRIEF DESCRIPTION OF THE DRAWINGS

FIG. 1 illustrates a perspective view of a screw driver, a material delivery probe and inner liner.

FIG. 2 illustrates a partially exploded perspective view of the screw driver and material deliver probe of FIG. 1, prior to connection to the pedicle screw.

FIG. 3 illustrates a cross-section view of FIG. 1. taken along line 3-3.

FIG. 4 illustrates an enlarged view of the distal end of the material delivery probe of FIG. 1 with counter-torque bar and gasket.

FIGS. 5a and 5b illustrate an inner liner that is inserted into the material delivery probe and screw driver of FIG. 1.

FIG. 6 illustrates a perspective view of an exemplary pedicle screw.

FIG. 7 illustrates a cross section view of pedicle screw of FIG. 6 taken along line 6-6.

FIG. 8 illustrates an insertion probe according for use in minimally invasive applications.

FIGS. 9 through 12 illustrate various other elements.

FIGS. 13a through 13c illustrate an insertion probe locked to a pedicle screw with a locking cam.

FIGS. 14a through 14c illustrate a set screw for securing an insertion probe to a pedicle screw.

FIGS. 15a through 15c illustrate an inflatable cuff for securing an insertion probe to a pedicle screw.

DETAILED DESCRIPTION

FIG. 1 shows a fluid delivery and bone screw driver apparatus 10. System 10 includes an inner shaft 15 (also referred to as a material delivery shaft), a screw driver or outer sleeve 20, and an inner liner 30. When system 10 is assembled, inner shaft 15 resides at least partially within outer sleeve 20. Inner shaft 15 and outer sleeve 20 can be secured to a pedicle screw 25, as will be described below. Inner liner 30 is received inside at least parts of both inner shaft 15 and outer sleeve 20.

Referring to FIGS. 2-4, inner shaft 15 has a proximal end 14 and a distal end 17. Proximal end 14 has a coupler, such as a threaded luer lock connection 16, for connection to a source of cementitious fluid. Distal end 17 has a counter-torque bar 18 and a gasket 19 that is shaped as an o-ring. Inner shaft 15 and outer sleeve 20 are made from stainless steel; however, they may be made from other metallic components having similar functionality. Gasket 19 is made from a non-metal pliable material capable of deforming and providing a seal between relatively moving components. Counter-torque bar 18 can be joined to the shaft by several methods, such as; welding, press-fit, gluing, or any other means known to those skilled in the art.

Inner shaft 15 has distinct markings or indicia 13 thereon near proximal end 14 that correspond to the position or orientation of fenestrations 33 on pedicle screw 25 shown in FIG. 2. Markings 13 serve to indicate to the surgeon the orientation of fenestrations 33 once the screw 25 is inside the body and can be used by a surgeon to align the screw 25 so as to direct cement to a particular location or direct the cement away from vital structures. Markings 13 can be machined, etched (chemical/laser), coated or inked on the inner shaft.

Referring to FIGS. 2, 3, 6 and 7, outer sleeve 20 has a threaded end 21 and a handle 22. Threaded end 21 has external threads thereon that are matingly received within threads 28 of pedicle screw 25. Handle 22 has two opposed ears that are configured for ease of handling and control when a physician is securing outer sleeve 20 to pedicle screw 25 and advancing pedicle screw 25. Pedicle screw 25 has a head 26 having a slot 29 therethrough. Slot 29 is configured to receive counter-torque bar 18 when inner shaft 15, outer sleeve 20 and pedicle screw 25 are assembled.

Referring to FIGS. 5a and 5b, inner liner 30 is received within inner shaft 15 and outer shaft 20 via luer lock connection 16 during use and is advanced distally through inner shaft 15 into screw 30. Liner 30 can be made of either metal, non-metal or a combination of both. Referring to FIG. 5b, liner 30 has a tapered distal end 31 that permits insertion into cannula 32 of screw 25. Liner 30 is inserted from 0.3 to 0.5 of the length of screw 25. Thus, the longer and larger the inner shaft of screw 25, the further liner 30 is inserted. Liner 30 is substantially inserted into screw 25 so that any reflux of cementitious fluid will stay within liner 30 and not flow through annular opening between pedicle screw 25 and inner shaft 15 past gasket 19. Liner 30 protects inner shaft 15 and outer sleeve 20 from cementitious fluid that may not stay inside of pedicle screw during fluid delivery. This is of particular concern because the cementitious fluid is often a highly viscous rapidly curing cement. The process of using liner 30 with inner shaft 15 and outer sleeve 20 will be discussed further below. Further, liner 30 is inexpensive disposable element.

Referring again to FIGS. 2,3,6 and 7, cross-section of pedicle screw 25 shows a seat 31, a cannula 32 and frenestrations 33. Outer sleeve 20 is able to rotate freely while captured on the inner shaft 15. When counter-torque bar 18 is received within slot 29, and gasket 19 is received within seat 31 of pedicle screw 25, the physician can rotate outer sleeve 20 relative to pedicle screw 25 which action compresses gasket 19 in seat 31. This compression ensures that a seal is created between gasket 19 distal end of inner shaft 15 and seat 31. The seal will prevent cementitious fluid from escaping from pedicle screw 25 during fluid delivery.

System 10 is connected to a fenestrated screw 25 via outer sleeve 20. Although not required, system 10 can be used with a conventional guidewire to advance system 10 to the desired location to commence procedure. Counter-torque bar 18 is placed in slot 29 and outer sleeve 20 is rotatingly joined to pedicle screw 25 via threads 28, thereby capturing inner shaft and securing sleeve 20 to pedicle screw 25. Once the surgeon has placed pedicle screw 25 in the desired location, the surgeon can then remove the guide wire (if one were used). Liner 30 is then inserted into proximal end 14 of inner shaft 15. After inserting liner 30, a cement reservoir or delivery tube is then connected to luer lock connection 16. After cement is delivered to the distal end of the pedicle screw 25, the entire assembly can be undocked from pedicle screw 25 with no other steps needed to achieve proper fixation. Once the cement has hardened, liner 30 can be removed and discarded, allowing the system 10, inner shaft 15 and outer sleeve 20 to be detached from pedicle screw 25 and reused.

Referring to FIGS. 8 through 12, system 100 does not use an outer sleeve. In contrast system 100 uses a probe 120 that has a gripping surface 122 to enable a surgeon to firmly grip and manipulate probe 120 during use at proximal end. Distal end of probe 120 has external threads 121 and gasket 119 as disclosed above. Probe 120 also incorporates a threaded luer connection 116 at proximal end to receive liner 30 therein Pedicle screw 125 has a rounded head that fits into a cap 126, such as shown in FIGS. 11 and 12. The rounded head enables rotation of pedicle screw 125 inside of cap 126. Gasket 119 is connected to distal end of probe 120 as shown at FIG. 8. Cap 126 is internally threaded to receive external threads 121 of probe 120. As probe 120 is rotated and advanced distally within cap 126, gasket 119 is compressed between pedicle screw 125 and probe 120.

Not using a torque bar in this embodiment finds use in minimally invasive spinal surgeries due to its small profile. System 100 can also use a liner 30 having the taper in the same way as system 10, described above. The minimally invasive configuration may not necessarily use a guidewire.

FIGS. 13a and 13c show an alternative to the threaded engagement of probe 220 and pedicle screw 225. Distal end of probe 220 has cam ears 221 that are received inside of recessed track 228 of cap 226. A ¼ turn locking cam ears 221 to hold cap 226 in place. A sealed connection is formed between gasket 219 and pedicle screw 225 to prevent leakage of cementitious fluid from pedicle screw 225 during delivery.

FIGS. 14a through 14c attaches the probe to the screw, wherein a set screw 310, is used. Set screw 310 having cam ears 315 is inserted into cap 326 along tracks 328. Set screw 310 uses a ¼ turn locking cam to wedge screw 310 into place. Probe 320 is threadingly received inside of set screw 310 and is advanced distally into pedicle screw 325. Gasket 319 is received on distal end of probe 320. Like earlier embodiments, gasket 319 is compressed to ensure a sealed connection between gasket 319 and the seat of pedicle screw. A liner 30 having a taper as described above can be used to prevent any damage to probe 320.

Referring to FIGS. 15 through 15c, a further system for securing probe inside of a pedicle screw is shown and generally referenced as system 400. System 400 includes a probe 420 and a liner 430 (which can be identical to liner 30) that are secured to a pedicle screw 425. System 400 has a sleeve 418 and an inflatable cuff 440. Sleeve 418 is connected to a pump, syringe, or other fluid source 417 via a tube or port 416 and transports fluid to inflatable cuff 440. Cuff 440 may be inflated by many substances, such as for example, air, water or saline solution. Cuff 440 is expanded inside of head of pedicle screw 425 to ensure that probe 420 is held securely in place during delivery of cementitions fluid.

The foregoing description has discussed only a few of the many forms that this invention can take. It is intended that the foregoing detailed description be understood as an illustration of selected forms that the invention can take and not as a definition of the invention. It is only in the claims, including all equivalents, that are intended to define the scope of this invention.

What is claimed is:

1. A fluid delivery and bone screw driver apparatus that attaches to a bone screw, the bone screw having a head with a slotted opening therein and a shaft with a cannula and fenestrations, the apparatus comprising:
   an outer sleeve having a first proximal end and a first distal end and comprising,
      external threads near the first distal end;
      a grasping surface near the first proximal end;
   an inner shaft extending through the outer sleeve, wherein the inner shaft has a second proximal end and a second distal end and comprises,
      a coupler at the second proximal end;
      a counter-torque bar at the second distal end wherein, when engaged with the bone screw head, the counter-torque bar extends radially through the slotted opening in the bone screw head, wherein the counter-torque bar further extends outwardly past the outer sleeve so that it can be manually rotated, and wherein the outer sleeve is independently rotatable around the inner sleeve;
      a gasket at the distal end; and
   a removable liner that extends through the proximal end of the inner shaft and out of the distal end of the inner shaft.

2. The apparatus of claim 1 wherein the inner shaft is longer than the outer sleeve and extends out of the first proximal end of the outer sleeve and the first distal end of the outer sleeve.

3. The apparatus of claim 2 wherein the outer sleeve is captured between the coupler and counter-torque bar.

4. The apparatus of claim 1 wherein the gasket is disposed around the outer surface of the inner shaft.

5. The apparatus of claim 1 wherein the grasping surface comprises a handle extending radially from the outer sleeve.

6. The apparatus of claim 1 wherein the external threads mate with internal threads in the head of the bone screw.

7. The apparatus of claim 6 wherein when the counter-torque bar is positioned in the slot of the screw head, the gasket is seated at the entrance of the cannula of the screw, the external threads are rotateably engaged with the internal threads in the head of bone screw; and wherein rotation further engages the external threads with the internal threads forcing the distal end of the inner shaft deeper into the head of the screw thereby compressing the gasket, and wherein further rotation causes the bone screw to rotate.

8. The apparatus of claim 1 wherein the liner has a tapered distal end that extends out of the second distal end of inner shaft and into the cannula of the bone screw.

9. The apparatus of claim 1 wherein the liner is disposable.

10. The apparatus of claim 1 wherein the couple comprise at least one of a luer lock and threads.

11. The apparatus of claim 1 wherein the inner shaft comprises markings that indicate the orientation of the fenestrations of the bone screw.

12. The apparatus of claim 1 wherein the inner shaft and outer sleeve are comprised of stainless steel.

13. The apparatus of claim 1, wherein the counter-torque bar can be manually rotated greater than 360 degrees.

14. A fluid delivery and bone screw driver apparatus that attaches to a bone screw, the bone screw having a head and a shaft with a cannula and fenestrations, the apparatus comprising:

an outer sleeve having a first proximal end and a first distal end and comprising,
   external threads near the first distal end that mate with internal threads in the head of the bone screw;
   a handles near the first proximal end;
an inner shaft extending through the outer sleeve, wherein the inner shaft has a second proximal end that extends out of the outer sleeve and a second distal end that extends out of the outer sleeve and comprises,
   a coupler at the second proximal end that connects to a material delivery source;
   markings at the second proximal end to indicate the position of the fenestrations;
   a counter-torque bar at the second distal end that is engageable in slots of the screw head, wherein the counter-torque bar extends past the outer sleeve;
   a gasket at the second distal end that is seated at the entrance of the cannula of the screw; and
a removable liner that extends through the second proximal end of the inner shaft and out of the second distal end of the inner shaft and into the cannula of the bone screw.

* * * * *